United States Patent [19]

Pratt, Jr.

[11] 4,233,845

[45] Nov. 18, 1980

[54] METHOD OF ASSESSING PERFORMANCE POTENTIAL OF A QUADRUPED

[75] Inventor: George W. Pratt, Jr., Wayland, Mass.

[73] Assignee: Massachusetts Institute of Technology, Cambridge, Mass.

[21] Appl. No.: 928,654

[22] Filed: Jul. 28, 1978

[51] Int. Cl.³ .............................................. G01D 21/00
[52] U.S. Cl. ..................................... 73/432 R; 119/29
[58] Field of Search ...................... 73/432 R, 379, 172; 119/29

[56] References Cited

U.S. PATENT DOCUMENTS 3,999,611   12/1976   Bucalo ..................................... 272/5

OTHER PUBLICATIONS

Science vol. 150, Nov. 5, 1965, pp. 701–708. Hildebrand, M. Symetrical Gaits of Horses–copy in Scientific Library.
Science vol. 151, Jan. 14, 1966, pp. 152, Geddes–letter re above article.

Primary Examiner—S. Clement Swisher
Attorney, Agent, or Firm—Arthur A. Smith, Jr.; Robert Shaw

[57] ABSTRACT

A method of assessing performance potential of a quadruped by determining the timing of successive making and breaking of ground contact by the legs during the stride and the swing time of a leg of the quadruped while in a high-speed gait. Overlap time of the legs, that is, the time that more than one leg is on the ground at one time, as a function of the forward speed of the quadruped and the time required to complete the stride are derived. The total airborne time is determined and related to the stance, swing, and overlap of the stride time. Performance is assessed in terms of swing time, stance time, overlap time, airborne time and combinations thereof. A method is disclosed of relating measurements of the gait taken at an arbitrary speed to a standard reference speed for purposes of comparing different individuals.

12 Claims, 5 Drawing Figures

METHOD OF ASSESSING PERFORMANCE POTENTIAL OF A QUADRUPED

The present invention relates to methods of assessing performance potential of quadrupeds in terms of high-speed gait.

By way of background, attention is called to a journal article entitled "A Relationship Between Gait and Breakdown in the Horse" (Pratt, Jr., et al), *The American Journal of Veterinary Research*, Vol. 39, No. 2, February, 1978, pp. 249–253, that discusses concepts of the present inventor and to a further journal article entitled "How Your Horse Gallops" (Pratt, Jr.), *Practical Horseman*, June, 1978, pp. 38–45 and 48.

A biomechanical model of running has been developed by the present inventor that when applied to a quadruped allows a prediction to be made of the performance potential of the animal with particular application to racing ability. A basic assumption of the model is that the swing phase time of the gait is essentially independent of the speed of the animal. The swing phase for a leg is the part of the stride during which said leg is not in contact with the ground. It is the preparation time during which a given leg is prepared for its next ground contact. The stance phase of a leg is the part of the stride during which said leg makes ground contact. The stride at any gait is the basic repeating sequence of leg and body motion of the horse and the gait is defined by the details of said repeating sequence. A stride-by-stride analysis of the motion of the horse is developed, based on the constant swing-time premise. The results agree well with actual performance. The performance potential of the horse as well as that of the racing dog is shown to depend on the length of time during a stride that two or more legs are simultaneously in ground contact, this being defined as the overlap phase of the gait, and to further depend on the length of time during the stride that all four legs are simultaneously not in ground contact, this being defined as the airborne phase of the gait. The length of the stride at any speed is shown to be related to the swing time and stance time. Furthermore, the swing time is related to the distance at which a quadruped can most effectively compete. The risk of breakdown is found to be related to the degree of extension in the gait. This, in turn, is determined by the precise timing of the individual legs both in making and breaking ground contact. As the speed increases, the horse must prolong his airborne time or increase his extension (or both) in order to provide this unchanging preparation time. The maximum safe speed at which the horse can run is related to the maximum vertical force that can be developed by the leading foreleg and the degree of extension in the stride. Although the discussion given herein deals primarily with the horse, the same concepts apply to any quadruped in particular the greyhound dog.

If the horse exceeds his maximum safe speed, then the requisite swing time cannot be maintained and the legs will prematurely contact the ground with consequently higher impact forces. The biomechanics of the swing phase, emphasizing the importance of properly controlling the speed of the leg at ground impact, was discussed by Rooney et al ("Biomechanics of Lameness in Horses," Baltimore Williams and Wilkins Co., 1969, pp. 46-48) and Cheney et al ("Cannon bone fracture in the thoroughbred racehorse," Med. Biol. Eng. 4:613-620, (1973)) who have shown that the bones of the horse suffer a substantial decrease in strength as a result of cyclical loading. The breaking strength of the cannon bone can drop to a level very close to the force predicted by the model presented subsequently. Experimental results obtained by the inventor show that weakening of the 3rd metacarpal or metatarsal (cannon) bone can be detected in vitro by measuring the elastic properties of the leg; for example, measuring velocity and attenuation of sound. In vivo measurements have been carried out.

Accordingly, it is an object of the present invention to provide a method of assessing the capability of a quadruped as that capability relates to the potential of that quadruped to engage in a high-speed gait.

Another object is to provide a method of determining at what distance the gait of a quadruped is most suited for maximum average speed.

Another object is to assess the prospects of the quadruped to compete without injury due to factors related directly to the nature of the gait of said quadruped.

Another object is to present means for determining the timing of the legs during a particular gait.

Another object is to determine the timing of the gait of a quadruped at a standard reference speed from measurements taken on said quadruped at an arbitrary speed and to characterize the gait at the reference speed by a set of parameters which include the overlap time of the stride at the reference speed. It is a further object to maintain a library of the gait parameters of like quadrupeds for the purpose of associating actual competitive performance with the parameters that define the gait.

Still further objects are addressed hereinafter.

The foregoing objects are achieved, generally, by a method of assessing the performance potential of a quadruped, that comprises the steps of determining the timing of successive making and breaking of ground contact by the legs during the stride of the quadruped while the quadruped is in a high-speed gait, determining the swing time of each leg of the quadruped while in said high-speed gait, deriving overlap time of the legs of the quadruped as a function of the forward speed of the quadruped and the time required to complete the stride, determining the total airborne time of the quadruped, relating the airborne time to the overlap time, and assessing the performance potential in terms of the overlap time, the airborne time, and a combination thereof. A less precise means of analyzing the gait is based on measuring only the ground contact times. Using data relating the average duration of the stance phase time for a leg as a function of the speed of the quadruped and combining this with the actual time of the individual footfalls, it is possible to derive all of the timing details of the stride, i.e., the overlap time, swing time, airborne time, and time duration of the stride. Ground contact times can be measured acoustically either by an acoustic sensor carried on the horse or by sensing the ground noise associated with the moving quadruped. For example, a simple tape recorder with appropriate microphone can be carried on the animal or a microphone adapted to pick up the sequence of acoustic signals generated by successive ground contacts of the legs.

The invention is hereinafter described with reference to the accompanying drawing in which.

of 3 months is noteworthy in that it supports the position that the timing of the legs is primarily an inherent characteristic of the horse.

Figure 2:
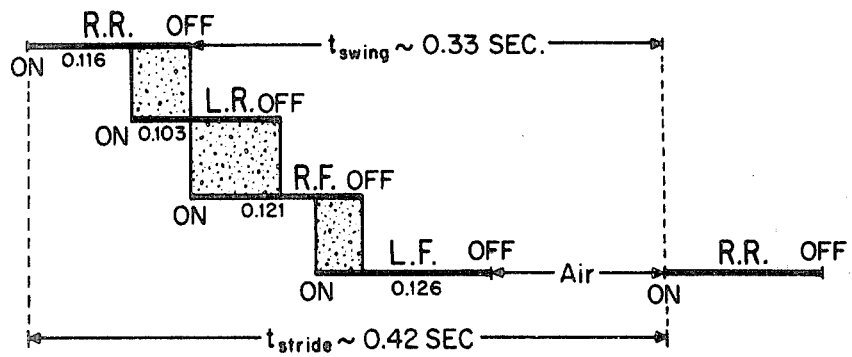
FIG. 2 is a graph, similar to FIG. 1, but for a horse having less capability than either horse represented in the graph of FIG. 1.

As a comparison with a more ordinary racehorse, the results of a frame-by-frame analysis of an unidentified horse taken at 485 frames/s are shown in FIG. 2 and listed in Table 1. Using Secretariat as a standard, the marked difference is the greater degree of overlap or comparatively poorer extension in the unidentified horse.

TABLE 1

Comparison of Strides of Secretariat and Riva Ridge

| Variant | Secretariat, Marlboro Cup Race | Secretariat, Belmont Race | Riva Ridge, Marlboro Cup Race | Another Horse |
|---|---|---|---|---|
| Average stance time (s) | 0.099 | 0.098 | 0.107 | 0.112 |
| Average swing (s) | 0.337 | 0.333 | 0.318 | 0.333 |
| Average total overlap (s) | 0.081 | 0.080 | 0.115 | 0.130 |
| Average airborne (s) | 0.121 | 0.125 | 0.115 | 0.123 |
| Average stride time (s) | 0.436 | 0.431 | 0.425 | 0.445 |
| Length of stride (m) (See equation 6) | 7.38 (24'3") | 7.38 (24'2") | 6.66 (21'10") | 6.66 (21'10") |

High-speed, slow-motion pictures of horses taken under racing conditions have been examined. In particular a frame-by-frame analysis was made of the Marlboro Cup race (Sept. 15, 1973) during the interval that Secretariat caught and passed Riva Ridge, as both horses went on to break the world record for 1⅛ miles. Of special interest was the question of how Secretariat's superior performance shows up in a comparison of the gaits. The sequence examined covers some 6 strides in 565 frames with both horses on a left lead. Averaging the frame count over the 6 strides and taking the film speed to be 200 frames/s produces the results shown in FIG. 1.

Figure 1:
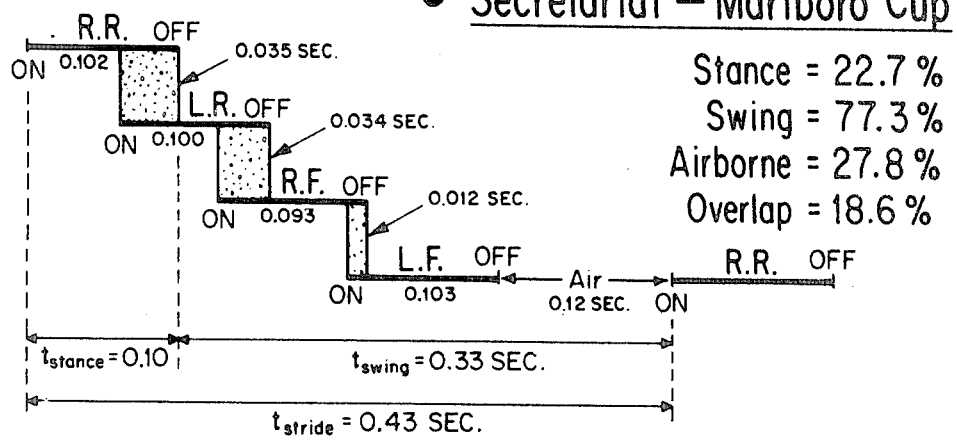
FIG. 1 is a graph showing the timing of the strides of Secretariat and Riva Ridge as the two horses approached the finish line during the running of the Marlboro Cup, Sept. 15, 1973.
Figure 1:
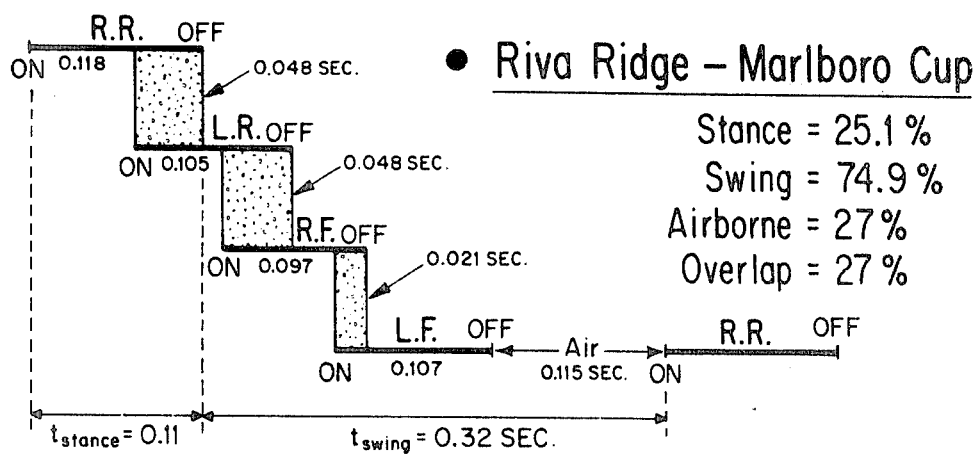

The swing time for any leg can be seen from FIG. 1 to be made up of the airborne time, $t_{air}$, plus the sum of the stance phase times of the other legs, but decreased by the periods during which 2 legs are on the ground at the same time. Herein this is called the overlap of the legs. In FIG. 1, the overlap periods are shown as cross-hatched areas. Thus, for the left lead, the swing time for the right rear leg is $$t_{swing} = t_{air} + t_{stance}(LR + RF + LF) - t_{overlap}(RR/LR + LR/RF + RF/LF) \quad (1)$$

The last term in equation (1) is denoted as the total overlap. A similar film showing Secretariat's performance near the end of the Belmont race (June 9, 1973) was also analyzed. The results are shown in Table 1. The times given in Table 1 assume a true film speed of 200 frames/s. Secretariat has the longest swing time, the smallest overlap, and the longest stride. A time difference of 0.01 seconds in stride time is equivalent to approximately 0.17 m/stride, or about 11 lengths in 1.2 km (¾ mile). It has been discovered by the present inventor that the optimum gait has the minimum overlap time. This can be understood since the net forward movement gained from a pair of legs that come down in succession is the sum of the forward travel on each separate leg minus the distance traveled while both legs are on the ground at the same time. The smaller the overlap, the greater the distance covered by successive steps. Small overlap is equivalent to large extension and an energy efficient stride. Secretariat shows a remarkable degree of extension. The close agreement in the different phases of the gait for Secretariat over a period The relationship of the observations in the preceding paragraphs to the problem of breakdown is now discussed. It has been suggested that the swing phase of the gait may be approximately independent of how fast the animal is going. In addition, the timing of the stride may originate in nerve centers in the spine and not be controlled by an active thought process but rather by events, i.e., by making or breaking contact of a leg with the ground. This suggests that the swing time and the degree of overlap at a given speed are built-in characteristics of the horse, only slightly affected by training or condition.

The individual stance phase times in equation (1) are now replaced for simplicity by an average stance phase time $$t_{stance} = l/v \quad (2)$$

where l is the distance traveled during the ground contact time of a leg. Since, at approximately 16.75 m/s, $t_{stance}$ is observed to be about 0.1 s, l is about 1.68 m. Using this result, one can rewrite equation (1) for the gallop as $$t_{swing} = t_{air} + 3l/v - t_{overlap} \quad (3)$$

Equation (2) shows that as the speed v increases, the stance time decreases. Therefore, in order to keep $t_{swing}$ constant, $t_{air}$ must increase or $t_{overlap}$ decrease, or both must occur.

It is remarkable that the notion of a constant swing time, independent of velocity, even extends to the same swing time for different gaits. A trotter or pacer has a swing time within a few hundreths of a second of that of a racehorse at the gallop. At the trot or pace, the legs move in pairs, the members of the pair almost completely overlapping in their action. However, the trotter or pacer does not move with the complete overlap of the pairs of legs that appear to move in unison. Indeed, it is the ability of the superior runner to decrease the overlap of these legs that greatly contributes to his performance. The total overlap time for each pair is close to the pair stance time $l/v$ and the total overlap per stride is, therefore, $2l - B/v$, where B is a correction factor. Furthermore, in the trot or pace, there are two airborne periods per stride. Consequently, $t_{swing}$ as given in equation 3 becomes $$t_{swing} = 2t_{air} + \left(\frac{3l}{v}\right) - \frac{2l-B}{v} = 2t_{air} + t_{stance} + \frac{B}{v}. \quad (4)$$

The stride time for gallop, trot, pace for any quadruped is $$t_{stride} = t_{swing} + t_{stance} \quad (5)$$

Knowing $t_{swing}$ and taking it to be independent for speed, using equation (2) for $t_{stance}$ while representing l as a linear function of speed, and accounting for the speed dependence of the overlap time, allows $t_{air}$ to be calculated at any speed using equation (3) for the gallop or by equation (4) for the trot, pace, or greyhound racing gait. This has been programmed and the graphics capability of the computer used to automatically produce graphical representations of the gait such as shown in FIG. 1 and FIG. 2 from the actual timing measurements made of the stride. The computer is further programmed to produce such a representation at any desired speed. The length of the stride is $t_{stride}$ times the velocity. The length of stride given in Table 1 was calculated from the easily derived relation:

$$l_{stride} = l\left(\frac{t_{stride}}{t_{stance}}\right) \quad (6)$$

A relationship is now derived between the airborne time, $t_{air}$, and the vertical force, $F_v$, that the horse must produce in order to achieve the assumed $t_{air}$. A ballistic flight is assumed, for example, in the gallop that begins when the lead fore hoof leaves the ground and ends when the opposite side rear hoof touches down. The $t_{air}$ is $$t_{air} = 2v_{oy}/g \quad (7)$$

Where $v_{oy}$ is the initial upward velocity and g is the acceleration of gravity. Force plate measurements indicate that the launching force acts for a fraction k of the total stance time beginning near the vertical position of the leg and ending at lift off. Measurements reported by Rooney et al suggest a value of k about 0.45 for the horse at the gallop. (Data taken at higher speed, i.e., 14 m/s and, hence, more representative of racing speeds, have been reported by Ronney JR, Quaddus MA, Kingsbury HB: Technical Report No. 194, Department of Mechanical and Aerospace Engineering, University of Delaware, February, 1977. They find a peak vertical force slightly less than 2 W.) The average net vertical force acting for a time $kt_{stance}$, is equated to the vertical momentum at lift off. The total vertical force $F_v$ is the net force plus the body weight W.

One finds for the horse at the gallop that $$F_v = W + (mv_{oy}/kt_{stance}) = W[1 + (t_{air}/2kt_{stance})], \quad (8)$$

where k is taken to be 0.45. If, for the moment, it is assumed that $$t_{air} = t_{stance},$$

which is a typical result from film data, equation (8) produces a value of $F_v$ of approximately 2 W. This is indeed close to the value observed by Rooney et al.

A very important result can now be derived from equation (8). As the horse goes faster, $t_{stance}$ given by equation (2) decreases and the vertical force, $F_v$, increases. If $t_{air}$ also must increase in order to keep $t_{swing}$ constant, then $F_v$ increases by an even greater amount. Basically, the horse must get itself into the air more quickly as its goes faster, and this requires greater force, especially if it has to stay in the air longer so that it can provide the necessary $t_{swing}$.

Equations (2), (3), and (8) can finally be combined to give an expression for the speed of the horse in terms of the vertical launching force $F_v$, weight W, $t_{swing}$, and the overlap which can be shown to vary as A(v)/v, where A is a function of v. In fact, A is the total distance covered during a stride when legs are overlapping. In the canter gait A is substantially larger than at the gallop. Taking k in equation (8) as 0.45, the result is:

$$v_{safe} = (0.91/W\, t_{swing})[F_v + 2.33W - (1.11AW/l)], \quad (9)$$

where $v_{safe}$ is the speed at which the horse can run which allows the proper swing time. As an example, a 454-kg horse, whose swing time is 0.32× and which travels a distance l=1.68 m over each leg and which can develop a vertical total force of $1.1 \times 10^4$N, can run at a speed $v_{safe}$ of:

$$v_{safe} = 22.8 - 3.12A \text{ m/s}, \quad (10)$$

where A is the overlap distance that can be estimated from film data or from other recording means such as acoustic. For Secretariat, A is 1.34 m, giving a maximum safe speed for $1.1 \times 10^4$N maximum vertical force of 18.6 m/s (or a quarter mile in 21.6 s). However, a lesser horse with greater overlap in its gait, say with an A of 1.83 m, that can develop the same $1.1 \times 10^4$N thrust, has a maximum safe speed of 17 m/s. If this horse pushes its speed beyond this point, it cannot provide the necessary time to prepare itself for successive steps in the stride. The model thus produces a relationship between the nature of the gait and the maximum safe speed.

In order to compare a group of quadrupeds and estimate their performance potentials and establish a rank ordering, it is necessary to apply this biomechanical model to the timing data taken on the gait of each animal and thereby to estimate the gait characteristics of all animals at the same reference speed. For example, when high-speed photography is used it is necessary to determine from the film or some other means, the actaul speed of each animal and then to determine what the timing sequence of the stride would be at the reference speed. The reference speed generally used for thoroughbreds is 16.75 m/s, 13.4 m/s for standardbreds, and 15.24 m/s for greyhounds.

In order to determine whether the horse can push itself to speeds that make an adequate $t_{swing}$ impossible, the dependence of speed on the horizontal driving force $F_H$ must be looked at. A differential equation describing the linear motion of the horse has been derived. The result is:

$$[mdv/dt] = \gamma v^2 = F_H(t) \quad (11)$$

The equation states that the driving force $F_H$ produces acceleration dv/dt and counteracts the force $\gamma v^2$ that impedes the motion of the animal. This restraining force arises from the fact that when any leg is initially loaded, it is at an angle that produces a back-directed force which must act to slow down the horse. A leg can provide a forward force only in that part of the stance phase when the leg is beyond the vertical. The parameter $\gamma$ characterizes the losses particularly into the running surface, a high $\gamma$ value corresponding to a slow track. The driving force $F_H$ has been modeled as a constant part $F_o$ related to aerobic processes and an exponentially decreasing part $F_1e^{-t/\tau}$ relating to the depletion of anaerobic energy. This model yields a remarkably accurate description of the acceleration of the horse to peak velocity reached in 8 to 10 seconds of the manner in which he slows down. For example, a 454 kg horse whose anaerobic decay time is set at 30 s, capable of sustained force $F_o$ of 2,224 N, and whose peak force at t=0 is 3,692 N running on a surface with a $\gamma$ value of 9.34 $NS^2/m^2$ performs as shown in Table 2.

TABLE 2

Solution of Equation (1) Giving the Performance of a Horse Starting from Rest*

| t,s | v,m/s | x,m | F,N |
|---|---|---|---|
| 0 | 0 | 0 | 3,692 |
| 1 | 7.63 | 5.81 | 3,648 |
| 2 | 13.21 | 17.78 | 3,603 |
| 4 | 18.04 | 51.27 | 3.527 |
| 6 | 19.02 | 88.85 | 3,452 |
| 8 | 19.07 | 127.01 | 3,381 |
| 12 | 18.76 | 202.69 | 3,252 |
| 20 | 18.13 | 359.02 | 3,043 |
| 23 | 17.93 | 404.01 | 2,976 |
| 30 | 17.50 | 536.69 | 2,847 |
| 40 | 17.07 | 700.74 | 2,709 |
| 70.5 | 16.32 | 1207.92 | 2,482 |

The last column of Table 2 shows the horizontal force averaged over each stride.

An entirely equivalent description of the horses' motion can be given on a stride-by-stride basis. One can do this and build into it the assumption of a constant swing time. In the nth stride, the horizontal propulsive force is taken as $$F(t) = F_o + F_1 e^{-t_n/\tau}, \quad (12)$$

where $t_n$ is the time at the beginning of the n th stride and, as before, ] is the anaerobic time constant describing the depletion of that energy source. This driving force applied in the n th stride will act to increase the velocity by $$[F(t_n)/m]\Delta t_n \quad (13)$$

Where $\Delta t_n$ is the total time during the n th stride during which the force acts. From the data of Rooney et al, (the combination of $\gamma L/m$ in equation (17) will be called $\Gamma$ hereinafter) this is taken at 0.45 $t_{stance}$ for each leg, or 1.8 $t_{stance}$ for all 4 legs in the stride. Thus, $$\Gamma t_n = 1.8 t_{stance} = 1.8 l/v_n \quad (14)$$

The distance l covered during ground contact grows from an initial value of about 1 ml in the first few strides to approximately 1.68 m after the horse has "hit his stride" some 20 or more strides from the start. (An average l for all 4 legs is used instead of distinguishing between the forelegs and hindlegs.) To account for this lengthening, l in (14) will be replaced from the thoroughbred by $$l_n = 1.68 - 0.76 e^{-n/20} \quad (15)$$

1 has been found to have a small linear variation with speed for the thoroughbred running in the vicinity of 15.2 m/s. Opposing the action of the driving force are the forces due to the braking action of the track and the resistance of the wind. In equation (11), the restraining force of the track is taken to be the form $\gamma v_n^2$ and it will act for a time $\Delta t_n'$. The $\Delta t_n'$ must decrease with speed as $L/v_n$, where L is a characteristic braking a length which turns out to be about 0.8 m per leg. Finally, the force of wind resistance is:

$$F_{wind} = 0.04 v_n^2 \quad (16)$$

in newtons, assuming an 0.74 $m^2$ frontal area of horse and rider. This force acts during the entire stride. The velocity in the n+1st stride is related to that in the nth stride by:

$$v_{n+1} = v_n + (1.8 F_n t_{stance}(n)/m) - [(\gamma L/m) v_n] - [(0.04 v_n^2)/m] \cdot t_{stride}(n) \quad (17)$$

This is the fundamental equation. To solve it, one starts at the first stride assuming an initial velocity $v_o$ produced by the acceleration coming out of the gate $(F_o + F_1)/m$. The $t_{stance}(1)$ is given by $l_1/v_o$, and $t_{stride}(1)$ is obtained by adding the constant swing time to $t_{stance}(1)$. The length of the first stride is $v(1) \cdot t_{stride}(1)$. Substituting into equation (17) gives the velocity $v_2$ in the second stride. Knowing $v_2$ allows $t_{stance}(2)$ to be calculated from equation (2), and $t_{stride}(2)$ by $v_2$ gives the length of the second stride. The time at the end of the second stride $t_2$ is the sum of the first two stride times and the total distance covered is the sum of the lengths of the first two strides. The time $t_2$ is used to calculate the new force from equation (12). Continual iteration of equation (17) in this manner allows one to follow the details of the model on a stride-by-stride basis. These results will now be combined with the expression derived for $v_{safe}$ in equation (9).

One can compare the velocity as obtained from equation (17) with $v_{safe}$ given in equation (9). As the animal tires, $F_v(t)$ will, of course, decrease. Let the vertical force, in excess of the weight W, fall below its initial value $[F_v - W]$ by a factor equal to the ratio of the horizontal driving force at time t to its initial value, i.e., $$F_v(t_n) - W = [F_v(0) - W](F_o + F_1 e^{-t_n/\tau})/F_o + F_1) \quad (18)$$

This simply says that the phenomenologic representation of the effects of fatigue is taken to be the same for both horizontal and vertical components of force. Using $F_v(t_n)$ as given in equation (9), $v_{safe}(t_n)$ for the nth stride can be evaluated.

The entire analysis has been programmed on a PDP-11/03 computer and the model investigated for a range of the parameters that go into the model. These are the weight W, $F_o$, $F_1$, the anaerobic lifetime $\tau$, the track loss (track variant) factor $\gamma$, the maximum vertical force $F_v(0)$, and finally, the overlap A(v). In Table 3, a solution of the stride-by-stride analysis is presented every five strides, and in Table 4, the solution is given approximately every 200 m for 2 further sets of model parameters. In Table 3, the model constants were chosen as $F_o = 227$ kg, $F_1 = 136$ kg, $\gamma = 45$ s, $t_{swing} = 0.32$ s, $\Gamma = 0.0644$, $F_v(0) = 11,565$ N, and the overlap constant A = 1.52 m.

TABLE 3

Solution of Equation (17) by Iteration
Giving Stride-by-Stride Performance*

| $n_{stride}$ | time (s) | distance (m) | velocity (m/s) | $l_{stride}$ (m) | $v_{safe}$ (m/s) | force (N) |
|---|---|---|---|---|---|---|
| 5.00 | 2.80 | 22.00 | 13.72 | 6.07 | 18.35 | 3,491 |
| 10.00 | 4.96 | 54.44 | 16.48 | 6.95 | 18.23 | 3,431 |
| 15.00 | 7.05 | 90.03 | 17.59 | 7.31 | 18.11 | 3,376 |
| 20.00 | 9.12 | 126.85 | 18.00 | 7.45 | 18.00 | 3,324 |
| 25.00 | 11.19 | 164.24 | 18.18 | 7.49 | 17.89 | 3,274 |
| 30.00 | 13.25 | 201.72 | 18.18 | 7.50 | 17.79 | 3,227 |
| 35.00 | 15.31 | 239.16 | 18.12 | 7.47 | 17.70 | 3,182 |
| 40.00 | 17.37 | 276.48 | 18.03 | 7.45 | 17.61 | 3,140 |
| 45.00 | 19.44 | 313.64 | 17.92 | 7.41 | 17.52 | 3,098 |
| 50.00 | 21.51 | 350.62 | 17.81 | 7.38 | 17.44 | 3,059 |
| 55.00 | 23.58 | 387.43 | 17.70 | 7.34 | 17.36 | 3,022 |
| 60.00 | 25.66 | 424.06 | 17.59 | 7.31 | 17.28 | 2,986 |
| 65.00 | 27.73 | 460.52 | 17.49 | 7.27 | 17.21 | 2,951 |
| 70.00 | 29.81 | 496.81 | 17.38 | 7.24 | 17.14 | 2,918 |
| 75.00 | 31.90 | 532.94 | 17.29 | 7.21 | 17.07 | 2,887 |
| 80.00 | 33.98 | 568.92 | 17.19 | 7.18 | 17.01 | 2,857 |
| 85.00 | 36.07 | 604.75 | 17.10 | 7.15 | 16.95 | 2,828 |
| 90.00 | 38.16 | 640.43 | 17.01 | 7.12 | 16.89 | 2,801 |
| 95.00 | 40.26 | 675.98 | 16.93 | 7.09 | 16.84 | 2,775 |
| 100.00 | 42.35 | 711.39 | 16.85 | 7.07 | 16.78 | 2,750 |
| 105.00 | 44.45 | 746.68 | 16.77 | 7.04 | 16.73 | 2,726 |
| 110.00 | 46.55 | 781.85 | 16.69 | 7.02 | 16.68 | 2,703 |
| 115.00 | 48.65 | 816.89 | 16.62 | 7.00 | 16.64 | 2,681 |
| 120.00 | 50.76 | 851.83 | 16.56 | 6.97 | 16.59 | 2,660 |
| 125.00 | 52.87 | 886.66 | 16.49 | 6.95 | 16.55 | 2,640 |

*Tabulation every 5 strides.

The results shown in Table 3 indicate that the safe velocity is initially greater than the actual velocity, as it must always be, because the horse starts from rest. However, for this choice of parameters, the actual velocity exceeds $v_{safe}$ from the 20th stride at 9.12 s and 126.9 m to the start of the 115th stride at 48.65 s and 816.0 m—just over ½ mile. The use of a constant swing-time model is certainly consistent with the actual performance of a typical horse. Although it is customary to speak of the length of a certain horse's stride, the stride length actually varies, as shown from equation (6).

Actual measurements of the horizontal force during the course of a race or work are not yet available, nor is a measurement of the parameter $\gamma$ which describes the braking action of the track. Forces (as given in Tables 3 and 4) do produce the initial acceleration observed in film analysis which are the order of 8 m/s². However, the power output of the horse, given by the product of the force and the velocity produces outputs of the order of 37 kW which must be too large by a factor of about 5. Evidently, a good deal of the energy apparently lost due to the braking action in the stride is actually stored as in a compressed spring and is available in the next acceleration.

TABLE 4

The Numerical Solution of Equation (17) for the Velocity and the Solution of Equation (9) for $v_{safe}$, Using Different Overlap Distances A

| $n_{stride}$ | time (s) | distance (m) | velocity (m/s) | $l_{stride}$ (m) | $v_{safe}$ (5.25) (m/s) | $v_{safe}$ (4.50) (m/s) | force (N) |
|---|---|---|---|---|---|---|---|
| 30.00 | 13.24 | 201.72 | 18.18 | 7.50 | 17.56 | 18.27 | 3,227 |
| 58.00 | 24.83 | 409.43 | 17.63 | 7.32 | 17.07 | 17.79 | 3,000 |
| 85.00 | 36.07 | 604.75 | 17.10 | 7.15 | 16.71 | 17.43 | 2,828 |
| 114.00 | 48.23 | 809.89 | 16.64 | 7.00 | 16.41 | 16.12 | 2,685 |
| 143.00 | 60.47 | 1,011.21 | 16.58 | 6.89 | 16.18 | 16.89 | 2,576 |
| 172.00 | 72.76 | 1,209.53 | 15.99 | 6.79 | 16.00 | 16.71 | 2,492 |
| 202.00 | 85.53 | 1,412.22 | 15.76 | 6.72 | 15.86 | 16.57 | 2,425 |
| 232.00 | 98.34 | 1,613.00 | 15.59 | 7.67 | 15.75 | 16.47 | 2,376 |
| 262.00 | 111.18 | 1,812.30 | 15.45 | 6.62 | 15.67 | 16.39 | 2,338 |
| 293.00 | 124.47 | 2,017.08 | 15.35 | 6.59 | 15.61 | 16.26 | 2,309 |

When the velocity exceeds $v_{safe}$, the horse cannot provide himself with the swing time needed and his legs come in contact with the track too soon. As a result, the legs are subject to excessive forces leading to a greater risk of breakdown. Table 4 shows the solution of the model using parameters exactly as in Table 3, except that the overlap distance A has first been increased from 1.52 m to 1.60 m to give $v_{safe}(1.60)$ and then decreased to 1.37 m to give $v_{safe}(1.37)$.

Figure 3:
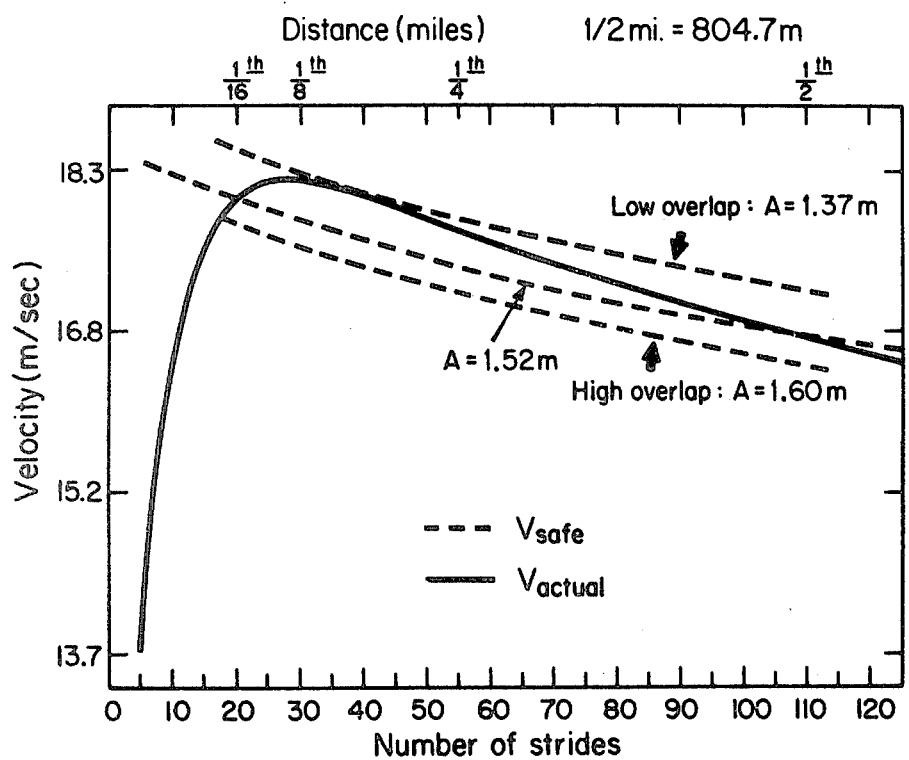
FIG. 3 is a graph showing the speed of a horse (solid line) plotted against the number of strides of the horse.

At an increased overlap, the velocity exceeds $v_{safe}$ for a full 1,207 m (or ¾ mile), whereas by dropping the overlap distance to 1.37 m, v never excees $v_{safe}$. At 16.8 m/s, the total overlap times are 1.60/16.8=0.0955 s and 1.38/16.8=0.0818 s. Thus, a difference of 0.014 s in overlap time is the difference between consistent overloading of the legs to never overloading them. These results are shown in FIG. 3 in which the actual velocity and $v_{safe}$ are plotted against the number of strides. The velocity, shown by the full line, peaks near 18.3 m/s and gradually decreases due to the depletion of anaerobic energy. The dependence of $v_{safe}$ on stride number is shown by the dotted curves, the uppermost of which corresponds to the smallest overlap distance A=1.37 m, the middle curve has A=1.52 m, and the lowest $v_{safe}$ curve corresponds to A=1.60 m. This figure shows how a horse capable of good extension has a higher margin of safety. Although this discussion has been given for the thoroughbred, the same analysis can be made for the trotter or pacer making the changes appropriate for the particular gait.

The time of maximum stress on the legs (i.e., when the velocity exceeds $v_{safe}$ by the largest margin) occurs shortly after 30 strides, or approximately 201 m or 1 furlong. The greater the difference berween v and $v_{safe}$, the longer the danger period lasts. The $v_{safe}$ as given in equation (9) does not depend on the track variant $\gamma$. A slower track (i.e., larger value of $\gamma$ in equation (17) acts to prevent v from exceeding $v_{safe}$ and, if other injury mechanisms do not appear, would be a safer track. This model does not include the extra stresses encountered in a turn. Their importance has been emphasized by Fredricson and Drememo.

Cheney et al have shown that the force on the cannon bone may be three to four times the force of the hoof on the ground due to the lever-type action of the fetlock joint. Under a single loading, the breaking strength of the cannon bone in vitro is approximately $71 \times 10^3$N. The present model suggests peak forces in the range of $11 \times 10^3$N on the hoof, which translates to $33 \times 10^3 \times 10^2$N on the cannon bone. However, Cheney et al have found that repeated loading reduces the strength of the cannon bone by some 40% over a period of 4,000 cycles, which could be produced by 10 races. Similar results have been observed in the tibia of living rats. If this were true of the living system, the breaking strength could drop to $43 \times 10^3$N, which is very close to the forces expected from the present model. In the living system, there is a tendency to strengthen bone in the regions of greatest stress. The fatigue weakening of the bone takes place over a much shorter period than that required for the strengthening process to occur. Consequently, if sufficient recovery time is not allowed for a horse that runs at speeds exceeding his safe speed for a great part of the time, then his supporting bones can be expected to drop in strength to the point where the normal loads experienced in racing will cause fracture. The elastic modulus of bone is known to decrease as it weakens as a result of cyclic loading. The present inventor has discovered that this process can be monitored by measuring the velocity of sound across the leg. Measurements on the metacarpal and metatarsal bones at 0.5 MHz, 1 MHz, and 2.25 MHz indicate a drop in sound speed across the proximal, distal, and midshaft portions of said bones. A drop by 10 percent has been found to exhibit a high correlation with subsequent fracture.

It may be possible to detect in vivo the reduction of strength of supporting bones of the horse. The large reductions measured by Cheney et al implies a substantial change in the elastic properties which should affect the transmission of sound through the leg. Experiments are now underway to measure attentuation of sound before and after a race.

Figure 4:
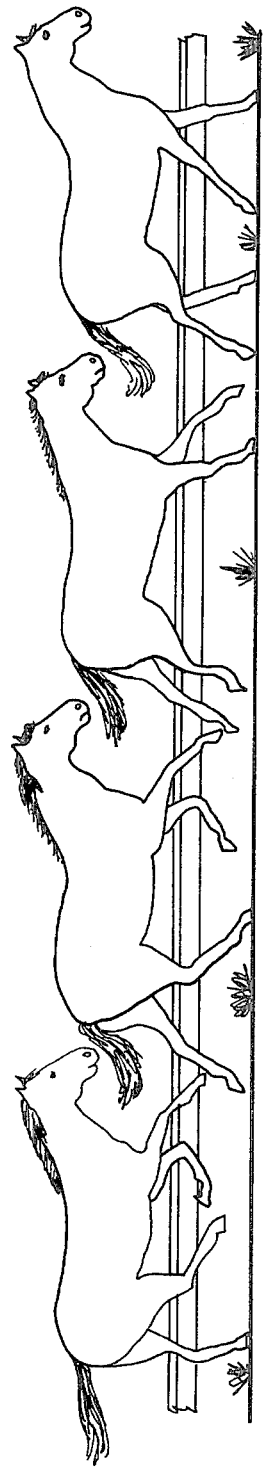
FIG. 4 shows a series of four views of a galloping horse.
Figure 5:
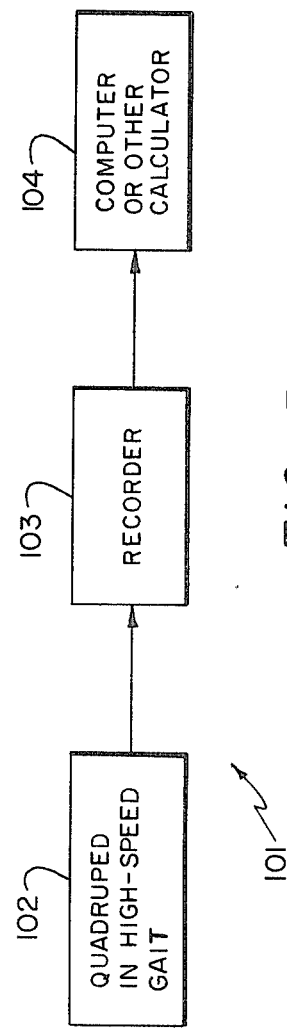
FIG. 5 shows in block diagram form a system to derive data and analyze the same in accordance with the present invention.

The views of the horse in FIG. 4 in four parts of a gallop may be taken by a recorder 103 in the system labeled 101 in FIG. 5 wherein the quadruped is designated 102. The recorder 103 in actual tests was in one instance a high speed camera and the data taken were analyzed using a computer 104 programmed in accordance with the foregoing teachings. In another instance, the data were taken by recording the sounds of the footfalls on a tape recorder fixed to the tack worn by the horse. The speed of the horse was determined by measuring the time required to travel a known distance. The average stance time was approximated as a linear function of speed. Knowing the stance times, the speed and the time of each footfall allows all of the timing details of the gait to be found. The tape recorder 103 was played into an analog-to-digital converter and the digital data used as input data for the computer 104. Yet another means of recording the footfalls is to couple a microphone or acoustic transducer to the ground to pick up and record the impacts of the legs with the ground.

The analysis given here for the thoroughbred is easily extended to the horse at different gaits as discussed, for example, in connection with equation (4). The greyhound runs with two airborne periods in his stride, one launched by the rear legs and one by the front legs. The lower the overlap of the hind legs and of the front legs, the less time the greyhound is required to spend airborne. The airborne phase of all gaits of all the quadrupeds is associated with high energy consumption. Low overlap in any gait decreases the fraction of the time of the stride during which the animal is airborne.

Further modifications of the invention herein disclosed will occur to persons skilled in the art and all such modifications are deemed to be within the scope of the present invention.

What is claimed is:

1. A method of assessing the performance potential of a quadruped, that comprises:
   causing the quadruped to move at a high speed gait;
   determining the timing of successive making and breaking of ground contact by the legs of the quadruped during its stride in said gait;
   measuring the overlap time during said stride;
   measuring the speed of said gait;
   and producing and displaying an output dependent upon the overlap time at said speed.

2. A method in accordance with claim 1, wherein the overlap time measured at said high speed is then converted to an overlap time at a reference speed.

3. A method in accordance with claim 2, wherein the steps recited are performed for each of a plurality of quadrupeds, respectively, and the outputs are compared.

4. A method in accordance with claim 1, wherein the quadruped is a horse and is caused to move at a gallop.

5. A method of assessing the performance potential of a quadruped, that comprises:
   causing the quadruped to move at a high speed gait;
   determining the timing of successive making and breaking of ground contact by the legs of the quarduped during its stride in said gait;
   measuring the airborne time during said stride;
   measuring the stride time;
   measuring the speed of said gait;
   and producing and displaying an output dependent upon the airborne time and the stride time at said speed.

6. A method in accordance with claim 5, wherein the airborne time and the stride time measured at said high speed are then converted to airborne and stride times, respectively, at a reference speed.

7. A method in accordance with claim 6, wherein the steps recited are performed for each of a plurality of quadrupeds, respectively, and the outputs are compared.

8. A method in accordance with claim 5, wherein the quadruped is a horse and is caused to move at a gallop.

9. Apparatus for assessing the performance potential of a quadruped moving at a high speed gait, that comprises:
   means responsive to the successive making and breaking of ground contact by the legs of the quadruped during its stride in said gait for producing corresponding signals;
   means responsive to said signals for measuring the overlap time during said stride;
   means for measuring the speed of said gait;
   and means for producing and displaying an output dependent upon the overlap time at said speed.

10. Apparatus in accordance with claim 9, wherein the first-mentioned means comprises acoustic sensor means.

11. Apparatus for assessing the performance potential of a quadruped moving at a high speed gait, that comprises:
   means responsive to the successive making and breaking of ground contact by the legs of the quadruped during its stride in said gait for producing corresponding signals;
   means responsive to said signals for measuring the airborne time during said stride;
   means responsive to said signals for measuring the stride time;
   means for measuring the speed of said gait;
   and means for producing and displaying an output dependent upon the airborne time and the stride time at said speed.

12. Apparatus in accordance with claim 11, wherein the first-mentioned means comprises acoustic sensor means.

* * * * *